(12) United States Patent
France et al.

(10) Patent No.: US 9,476,159 B2
(45) Date of Patent: Oct. 25, 2016

(54) NON-DESTRUCTIVE EVALUATION OF FUNCTIONAL FABRICS

(71) Applicant: TDA Research, Inc., Wheat Ridge, CO (US)

(72) Inventors: Christopher Brian France, Arvada, CO (US); William Wallace Ellis, Louisville, CO (US); Brady Clapsaddle, Littleton, CO (US); William Bell, Boulder, CO (US); Ronald Cook, Lakewood, CO (US)

(73) Assignee: TDA Research, Inc., Wheat Ridge, CO (US)

( * ) Notice: Subject to any disclaimer, the term of this patent is extended or adjusted under 35 U.S.C. 154(b) by 0 days.

(21) Appl. No.: 14/664,107

(22) Filed: Mar. 20, 2015

(65) Prior Publication Data
US 2016/0273154 A1 Sep. 22, 2016

(51) Int. Cl.
*G01N 21/84* (2006.01)
*D06H 3/08* (2006.01)
*G01N 21/88* (2006.01)
*D06H 3/02* (2006.01)

(52) U.S. Cl.
CPC .................. *D06H 3/08* (2013.01); *D06H 3/02* (2013.01); *G01N 21/8806* (2013.01); *G01N 21/8851* (2013.01)

(58) Field of Classification Search
CPC . G01N 21/898; G01N 21/8983; G01N 21/55
USPC .................. 356/402, 429–431, 237.1–237.5, 356/445–448
See application file for complete search history.

(56) References Cited

U.S. PATENT DOCUMENTS

| | | | | |
|---|---|---|---|---|
| 4,103,177 A | * | 7/1978 | Sanford | G01N 21/8983 250/559.03 |
| 4,999,488 A | * | 3/1991 | Sollars | G01S 17/50 250/222.2 |
| 5,848,117 A | | 12/1998 | Urchuk et al. | |
| 6,716,775 B1 | * | 4/2004 | Dischler | D06C 11/00 28/160 |
| 8,609,428 B2 | | 12/2013 | Kaur et al. | |
| 8,923,595 B2 | | 12/2014 | Sokolov et al. | |
| 2002/0191189 A1 | * | 12/2002 | Mestha | G01J 3/02 356/402 |
| 2003/0081215 A1 | * | 5/2003 | Kumar | G01N 21/8983 356/431 |

(Continued)

OTHER PUBLICATIONS

American Associiation of Textile Chemicsts and Colorists (AATCC) Test Method 135-2004.

(Continued)

*Primary Examiner* — Hoa Pham
(74) *Attorney, Agent, or Firm* — Brian J. Elliott

(57) ABSTRACT

The present invention provides a method for determining the functionality remaining in a functional fabric, the method comprising the steps of: providing a used functional fabric having a known original functionality, a current wear, and a current unknown functionality, providing a light source, providing a detector, optically measuring the current wear using the light source and the detector, and evaluating the current unknown functionality using a correlation that expresses the current unknown functionality as a function of the current wear, optionally the detector further comprises a digital camera, and wherein the method further comprises the step of: obtaining a magnified image of the functional fabric and quantifying the fractal dimension using a box-method fractal analysis on the image. The method may be applied the insecticide treated fabrics.

18 Claims, 19 Drawing Sheets

(56) References Cited

U.S. PATENT DOCUMENTS

| | | | | |
|---|---|---|---|---|
| 2004/0188042 A1* | 9/2004 | Pylkki | ................ | E06B 9/52 160/371 |
| 2006/0251338 A1* | 11/2006 | Gokturk | ............ | G06F 17/30253 382/305 |
| 2007/0291252 A1* | 12/2007 | Berman | .................. | E06B 9/32 356/73 |
| 2014/0030741 A1 | 1/2014 | Ahn et al. | | |

OTHER PUBLICATIONS

American Associiation of Textile Chemicsts and Colorists (AATCC) Test Method 135-2004 American Associiation of Textile Chemicsts and Colorists (AATCC) Test Method 22-2005.

American Associiation of Textile Chemicsts and Colorists (AATCC) Test Method 124-2009.

Ulrich R. Bernier "Mosquito bite protection . . . " 59th Annual Meeting of the Entromological Soc. of Am., Nov. 13-16, 2011 (p. 22).

Who (2006)"Guidelines for Testing Mosquito Adulticides for Indoor Residual Spraying and Treatment of Mosquito Nets." WHO Pesticide Evaluation Scheme.

Green et al. (2009). "Rapid colorimetric field test to determine levels of deltamethrin on PermaNet® surfaces: . . . " Tropical Medicine and International Health 381-388.

Faulde et al (2006) "Factory-Based Permethrin Impregnation of Uniforms: . . . " Miltitary Medicine, 171 (6), 472.

\* cited by examiner

NON-DESTRUCTIVE EVALUATION OF FUNCTIONAL FABRICS

BACKGROUND

Functional fabrics may be produced or modified to provide a specific function. Herein we define a functional fabric as a fabric that is intended to provide a specific function. For example, functional fabrics may be used for water-repellent clothing, permanent press clothing, antimicrobial clothing, and clothing or bednets treated to kill or repel biting arthropods. Functional fabrics may have an additive when they are produced or may have an additive incorporated after they are produced. Functional fabrics can also be treated to produce or enhance the function; such a fabric will be referred to herein as a treated fabric. In a functional fabric the fabric and additive or treatment act together to produce the desired effect.

In use, functional fabrics can lose part or all of their function due to exposure to the environment, laundering, wear and abrasion. In a used functional fabric, it is desirable to determine the functionality remaining, so the user can decide whether to continue to use the fabric or replace it. Herein the term functionality means the level of function. The determination is preferably in the form of a quantitative assay, so the user can determine if the remaining functionality is satisfactory for the situation.

Methods to determine the remaining functionality either directly or indirectly quantify the functionality. In one case, test methods measure the desired function directly; for example, by testing the amount of water that penetrates a water-repellent fabric, or by assaying the effectiveness of an insect-protective garment using live biting insects. Such methods are often expensive, time-consuming, may damage the fabric or garment, and may require resources that are not readily available. In another case, a test method measures the remaining quantity of the additive used to impart the function; for example, in garments treated with permethrin for protection against insects, the permethrin may be extracted using a solvent and quantified by chemical analysis. Such methods can require reagents and analytical instruments that are not readily available in the field, may be expensive and time-consuming, and may damage the fabric or garment. Further, such methods only confirm that a specific additive is present, not that functional fabric performs its function. For example, the insecticide on a treated garment may be present, as determined by chemical analysis, but may not perform the desired function because it is not biologically available, or the fabric may be so worn that it does not form an adequate physical barrier.

Functional fabrics may suffer loss of function during normal use due to fabric wear and due to loss of the additive. Laundering may cause loss of function and is also a source of fabric wear. A practical method to assess the remaining functionality will desirably incorporate some indicator of fabric wear or abrasion.

A desirable method to assay remaining functionality would be simple, inexpensive, rapid, quickly carried out in a laboratory or in the field, require no consumable supplies, and not damage the fabric so that it could (if warranted) continue in use.

Current methods test only a section of the fabric. However, particularly in the case of water-repellent or insect-protective fabrics, if the functionality is not present everywhere in the fabric, then the function is compromised. For example, if a section of a garment is not water-repellent the wearer will get wet in that location. More seriously, if a section of an insect-protective garment does not retain its functionality, then the user could get bitten in that location, potentially acquiring a disease. Therefore, in addition to the desirable properties cited above, it is a further advantage of a simple and rapid assay that it can more readily be applied to multiple locations of the item being tested. For example, in the case of clothing, it could be applied to areas that are known to experience high wear (knees, elbows) and areas that appear to be worn or abraded.

An important example of functional fabrics is certain U.S. military uniforms that are treated with permethrin (a pyrethroid insecticide) to protect soldiers from arthropods that carry diseases, including malaria, dengue fever, and Lyme disease. Efficacy is measured by the bite protection test performed at the USDA Center for Medical, Agricultural, and Veterinary Entomology (CMAVE) in Gainesville, Fla. To pass the test, the uniforms must retain efficacy after 25 standard washes performed according to American Association of Textile Chemists and Colorists (AATCC) Test Method 135-2004. However, it has been found that uniforms worn in the field lose activity faster than predicted by the number of wash cycles they have been through. As shown in Bernier (Page 22 in Ulrich R. Bernier, "Mosquito Bite Protection of Factory-Level Permethrin-Treated United States Military Combat Uniforms" $59^{th}$ Annual Meeting of the Entomological Society of America, Nov. 13-16, 2011; incorporated by reference herein), test data on treated uniforms worn in Iraq shows that the level of bite protection does not correlate with the number of washings of the uniforms. Furthermore, some uniforms showed negative bite protection; in those cases, the bite protection afforded by the treated, field-worn uniform was less than that provided by a new, untreated uniform. The interpretation is that those uniforms were thinner due to field wear, likely both lacking permethrin and being thinner, thus allowing the insects to bite through the fabric. A treated uniform may need to retain both an effective amount of permethrin that is accessible to insects landing on the surface, as well as sufficient fabric thickness and structural integrity to provide a physical barrier.

Wear and abrasion are examples of mechanisms by which functional fabrics and treated fabrics may lose functionality. Further, as wear breaks down the uniform fibers, water can more easily penetrate and insects (including mosquitoes) can more easily bite the wearer through the fabric.

Existing methods to assess remaining functionality in treated fabrics either measure the property directly, or use a destructive surface sampling and chemical analysis to quantify the amount of remaining additive responsible for the function.

Examples of direct methods include: tests of water repellency, for example AATCC Method 22-2010, which is described as "applicable to any textile fabric, which may or may not have been given a water-repellent finish". It measures the resistance of fabrics to wetting by water. It is especially suitable for measuring the water-repellent efficacy of finishes applied to fabrics." In this test, "water sprayed against the taut surface of a test specimen under controlled conditions produces a wetted pattern whose size depends on the relative repellency of the fabric". Evaluation is accomplished by "comparing the wetted pattern with pictures on a standard chart". Similarly for permanent press fabrics, AATCC Test Method 124-1996 describes standard conditions to assess the "Appearance of Fabrics After Repeated Home Laundering," using standard conditions for laundering.

In the case of fabrics treated for protection from arthropod bites, the World Health Organization (WHO) cone test is a standard that requires exposure to live, host-seeking mosquitoes (WHO 2006). WHO cone tests were originally designed to evaluate the toxicity of insecticide-treated bednets against malaria mosquitoes. They are also suited to investigate the toxicity of other impregnated (textile) surfaces. The bite protection test performed by the Center for Medical, Agricultural, and Veterinary Entomology (CMAVE) also uses live mosquitoes (Bernier 2011). This test is used by the U.S. Army to assess the initial performance of their permethrin-treated uniforms.

Examples of destructive tests include: several methods to assess the remaining functionality of garments treated to protect against arthropod bites by sampling, followed by chemical analysis.

Kaur et al. (2013) describe sampling followed by colorimetric assay for pyrethroid insecticides on treated bednets and other items. This technology was developed by the Innovative Vector Control Consortium (IVCC) and has led to a product called the Insecticide Quantification Kit. Similarly, Green and co-workers at the Centers for Disease Control and Prevention (CDC) have described sampling procedures and colorimetric analysis for pyrethroids on surfaces, including fabrics (Green et al. 2009, 2013). The above methods rest on chemical analysis, which can be very specific to the additive (for example, a pyrethroid containing a cyano group); other additives may not respond to the analytical method, requiring development of new chemistry.

Ahn et al (2014) discloses novel chemistry for analysis of certain types of pyrethroids, further emphasizing the challenge of chemical analysis.

Fractal analysis has been used for a wide range of practical applications, such as in the medical field, including fractal analysis of cell images to distinguish between normal and cancerous cells; Bauer (1998) and Sokolov (2014).

These references contain at least one of the following limitations in regard to evaluating functional fabrics: inability to assay functionality non-destructively; requires reagents, solvents or specialized equipment that are not readily available; requires direct measurement of the function, for example live insect tests; is expensive, is inconvenient; or does not utilize fractal analysis to assay functionality.

There remains a need in the art for simple, non-destructive test to assay the functionality of used functional fabrics.

BRIEF SUMMARY OF THE INVENTION

The present invention relates to a method for evaluating functional fabrics and solves the limitations of the prior art.

One embodiment is a method for determining the functionality remaining in a functional fabric, the method comprising the steps of: (a) providing a functional fabric having a known original functionality, a current wear, and a current unknown functionality, (b) providing a light source, (c) providing a detector, (d) optically measuring the current wear using the light source and the detector, and (e) evaluating the current unknown functionality using a correlation that expresses the current unknown functionality as a function of the current wear. Optionally, the method further comprises the step of: (f) aligning the light source, the detector and the functional fabric and measuring the reflectance of the light source off of the functional fabric, wherein the light source [20] is aligned relative to the functional fabric [10] at a first angle [21], wherein the first angle is from 0 to 180 degrees; and wherein the detector [30] is aligned relative to the light source at a second angle [22], wherein the second angle is from 0 to 180 degrees, wherein the sum of the first angle plus the second angle is at most 180 degrees. In a separate embodiment the method optionally further comprises the step of: (f) aligning the light source, the detector and the functional fabric and measuring the transmittance of the light source through the functional fabric, wherein the light source [120] is aligned relative to the functional fabric [110] at a first angle [121], wherein the first angle is about 90 degrees; and wherein the detector [130] is aligned relative to the light source at a second angle [122], wherein the second angle is from −5 to 5 degrees, wherein the sum of the first angle plus the second angle is at most 180 degrees.

In certain embodiments the light source emits light with a wavelength from 10 nanometers to 100 micrometers, 10 nanometers to 400 nanometers, 700 nanometers to 100 micrometers, or essentially a single wavelength.

In another embodiment the optically measuring the current wear using the light source and the detector further comprises a color temperature measurement.

In yet another embodiment, the method comprises the additional step of measuring the transmittance of the light source through a reference material and quantifying the intensity or spectral distribution of the light source. The reference measurement may then be used in combination with a transmittance measurement of the functional fabric to quantify the functionality left.

In certain embodiments the functionality is insect repellency or mortality derived from an insecticide or an insect repellent, preferably the insecticide or insect repellent comprises a pyrethroid, more preferably permethrin.

In a preferred embodiment, the detector further comprises a digital camera, and wherein the method further comprises the step of: (f) obtaining an image of the functional fabric and quantifying the fractal dimension using a box-method fractal analysis on the image; optionally the method further comprising the step of: (g) aligning the light source, the detector and the functional fabric and measuring the reflectance of the light source off the functional fabric or: (g) aligning the light source, the detector and the functional fabric and measuring the transmittance of the light source through the functional fabric.

An embodiment of the invention is where the functionality is antimicrobial activity. The antimicrobial function may optionally be used in medical apparel to prevent healthcare-associated infections.

In an additional embodiment, the method for determining the amount of functional compound remaining in a functional fabric, the method comprising the steps of: (a) providing a functional fabric having a functional compound, a known original functional compound loading, a current wear, and a current unknown functional compound loading, (b) providing a light source, (c) providing a detector, (d) optically measuring the current wear using the light source and the detector, and (e) means for evaluating the current unknown functional compound loading using a correlation that expresses the current unknown functional compound loading as a function of the current wear-based damage. "Means for" is defined in the specification and the accompanying drawings herein.

Figure 1:
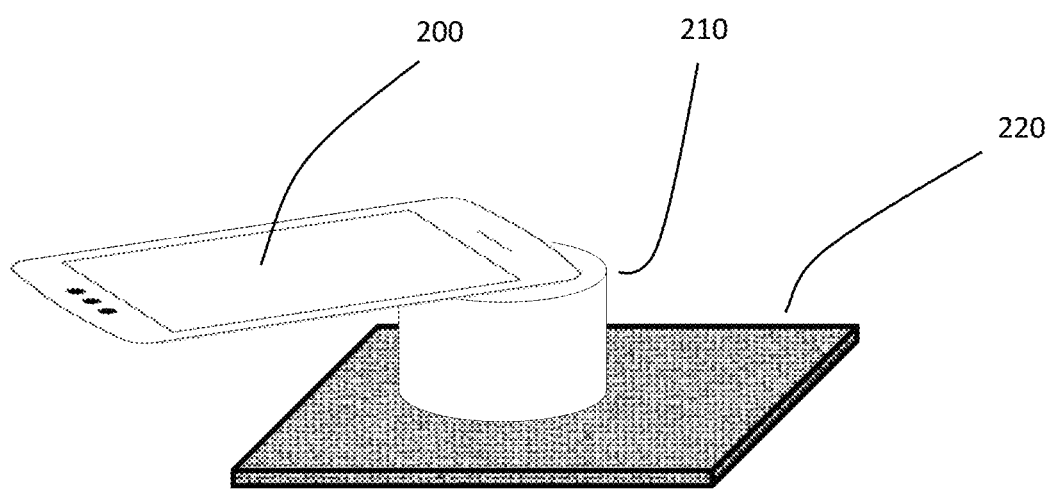
FIG. 1. Smartphone [200] with a commercially available micro-lens attachment [210] to image a field-worn MCCUU fabric sample [220].

The Brief Summary Of The Invention above and in the Detailed Description of the Invention, and the Claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The term "comprises" and grammatical equivalents thereof are used herein to mean that other components, ingredients, steps, etc. are optionally present. For example, and article "comprising" (or "which comprises") component A, B, and C can consist of (i.e. contain only) components A, B, and C, or can contain not only components A, B, and C but also one or more other components.

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending on the variable being defined). For example, "at most 4" means 4 or less than 4, and "at most 40%" means 40% or less than 40%. When, in this specification, a range is given as "(a first number) to (a second number)" or "(a first number)-(a second number)", this means a range whose lower limit is the first number and whose upper limit is the second number. For example 25 to 100 mm means a range whose lower limit is 25 mm, and whose upper limit is 100 mm.

Functional fabric means a fabric that provides a specific function.

Treated fabric means a fabric that has been treated to produce or enhance a function.

Functionality means the level of a function.

Wear is a general term describing the damage to or loss of material, for example loss of material from a fabric, or damage to the fibers that make up the fabric. Wear often occurs by rubbing two surfaces together. Abrasion is one non-limiting example of a process to cause wear. Wear in the specification and in the attached claims is meant to be a noun, as in the standard definition; the result of wearing or use: diminution or impairment due to use.

Luminance means the light intensity measured in unit of "Lux".

Color temperature means the temperature of an ideal black-body radiator which closely matches the color of the light source.

Full spectrum means substantially all of the wavelengths present in the light source.

The term posterize, and the related posterization or posterized, means a process known in the photographic and digital arts, and is generally defined as the conversion of an image having a continuous gradation of colors or greyscale to several regions of fewer tones, often only a small number of tones, with abrupt changes from one tone to another. This method was originally performed with photographic processes to create posters. It can now be done with digital processing software.

The present invention teaches that the functionality remaining in a functional fabric correlates with optical measurements. Optical measurements are defined as a measurement of the intensity of light that is either reflected from or penetrates through a fabric to be analyzed. Optical measurements are further defined as digital or photographic images that may optionally use magnification of the sample image. The light may be in the visible range or in the ultraviolet or infrared range in addition to the visible range. The measurement may use a broad range of wavelengths (e.g., all visible light) or a narrow range (e.g., 400 to 410 nm wavelength).

The present invention describes how optical measurements can be used to assay the proportion of the original functionality in a functional fabric that is remaining after wear. The present invention teaches a method comprising measuring the optical properties of samples of functional fabrics that are new and other samples that have been worn or used. These known samples are selected so that they represent a range including samples that are new, with 100% of the functionality present, and samples that are used or worn, with an functionality remaining that is less than or equal to the amount of functionality that is likely to be acceptable for continued use. In the present method, data for these reference samples provide a calibration curve that relates the optical measurement to the amount of functionality remaining. For using the method on an unknown fabric sample, the analogous optical measurement is made, and the functionality remaining is determined using the calibration data.

The optical measurement of this invention is not to be interpreted as a direct spectroscopic measurement of molecules used to impart functionality to a functional fabric. For example the optical measurement is not a direct measurement of the adsorption of infrared light by the chemical bonds of an insecticide, for example Fourier Transform Infrared Spectroscopy. Rather, the optical measurements of the present invention measures the wear of the functional fabric and indirectly assay the functionality remaining with the use of the correlation data.

In one embodiment the optical measurement is reflectance at a specific wavelength. For example 400 nm, see Example 1. In other embodiments a range of light wavelengths may be used: from 10 nanometers to 100 micrometers, from 10 nanometers to 400 nanometers, from 700 nanometers to 100 micrometer, from 10 nanometers to 100 micrometers, from 10 nanometers to 400 nanometers, from 700 nanometers to 100 micrometers, or the full spectrum of visible light from the sun.

Optical measurement are initially evaluated to determine the correlation with the functionality that is being measured. Optical measurement may be selected from: transmission, reflectance, or a combination of both, to give a satisfactory correlation. Optical measurements may also be digital images or photographs that are optionally enlarged or magnified.

In one embodiment, the optical measurement, for example a digital image, is first evaluated using fractal analysis. Fractal analysis is assessing fractal characteristics of data. It consists of methods to assign a fractal dimension and other fractal characteristics to a dataset which may be a pattern. For the present invention, fractal analysis assigns a fractal dimension and other fractal characteristics to a digital image, preferably an enlarged or magnified digital image of a functional fabric. More preferably the image has been digitally processed to form a pure black and pure white two-toned, or "posterized" image.

The functional fabrics of the present invention are generally worn as the outermost layer, and they are subjected to physical wear.

This invention teaches a method that comprises the step of evaluating the current unknown functionality using a correlation. To first obtain the correlation one can obtain and analyze fabrics that have been subjected to normal use and wear, to establish a reference for correlation. If this is not practical, then an artificial wear process, for example using abrasion, or by using repeated standard launderings, may be chosen to provide samples with known and reproducible levels of wear. The functionality remaining in a reference sample may be determined by measuring the desired property directly (e.g., AATCC methods, bite protection, etc.) or by measuring the amount of an additive remaining by chemical analysis.

The components to the measurement are a light source and a system for measuring the intensity of light or a system to record a digital image, optionally using ambient light. It is readily apparent that light sources may potentially include sunlight (indoors or outdoors), artificial light, such as incandescent bulbs, lasers, light-emitting diodes, and other sources of light in the visible, ultraviolet and/or infrared wavelengths. Filters may be used to select a specific range of wavelengths for the measurement from a light source comprising a broader range of wavelengths. The system for measuring the intensity of the light reflected from or passing through the sample may be a spectrophotometer or any instrument or device that produces a signal that is correlated to changes in light intensity. The intensity of light may be assessed by the human eye, optionality assisted by a chart of color or intensity. The light intensity measurement does not quantify light in the infra-red region that is absorbed by chemical bonds.

The correlation may be made by comparing the optical measurement with a value from a chart. This process may be assisted by a computer or similar device. Smartphones, which commonly incorporate a light source, a camera and a computer, could perform all of the functions.

It is understood that the correlation between the optical measurement and the functionality remaining will be valid for a specific fabric and a particular treatment. For a functional fabric with a different fabric or a different treatment, a new correlation must be determined.

In an embodiment, the method of the present invention uses non-destructive optical assessment of a fabric, for example a uniform, correlated to the measured bite protection and permethrin content of new and worn uniforms having the same fabric. In one embodiment, a correlation of the reflectance spectroscopy measurement is used to quantify fabric wear. In the examples below, field-worn treated Marine Corps Combat Utility Uniforms (MCCUUs) were characterized for both bite protection and permethrin content. In these examples reflectance spectroscopy, and two additional methods are demonstrated: (1) measurement of light transmission, and (2) fabric imaging with a low-power microscope followed by fractal analysis. Each of these methods may be used independently or in combination with any of the others to correlate the optical measurements with bite protection and permethrin content. In a preferred embodiment, the correlation uses a combination of fractal analysis and light transmission measurement. As described in detail below, both can be accomplished with a simple, compact, low-power apparatus, a non-limiting example is a smartphone [200] and a commercial off the shelf microscope lens [210] to image a functional fabric sample [220] (see FIG. 1). Fractal analysis and correlation can be executed using and suitable microprocessing device including a desktop computer, smartphones, and the like, so that the entire operation (imaging, analysis and result) could be carried out using either a combination of devices or a single device. For example, the camera image alone (with lighting from above from one image, lit from behind in another) can be used to determine the protective capacity of the uniform.

The following are non-limiting examples of the invention.

Example 1

U.S. military uniforms (Marine Corps Combat Utility Uniform) were acquired and abraded to artificially wear the fabric. Optical reflectance spectroscopy was performed on the worn samples to show how wear affects the fabric, and also how it can be used to quantified the amount of permethrin remaining on the worn fabric samples.

Figure 2:
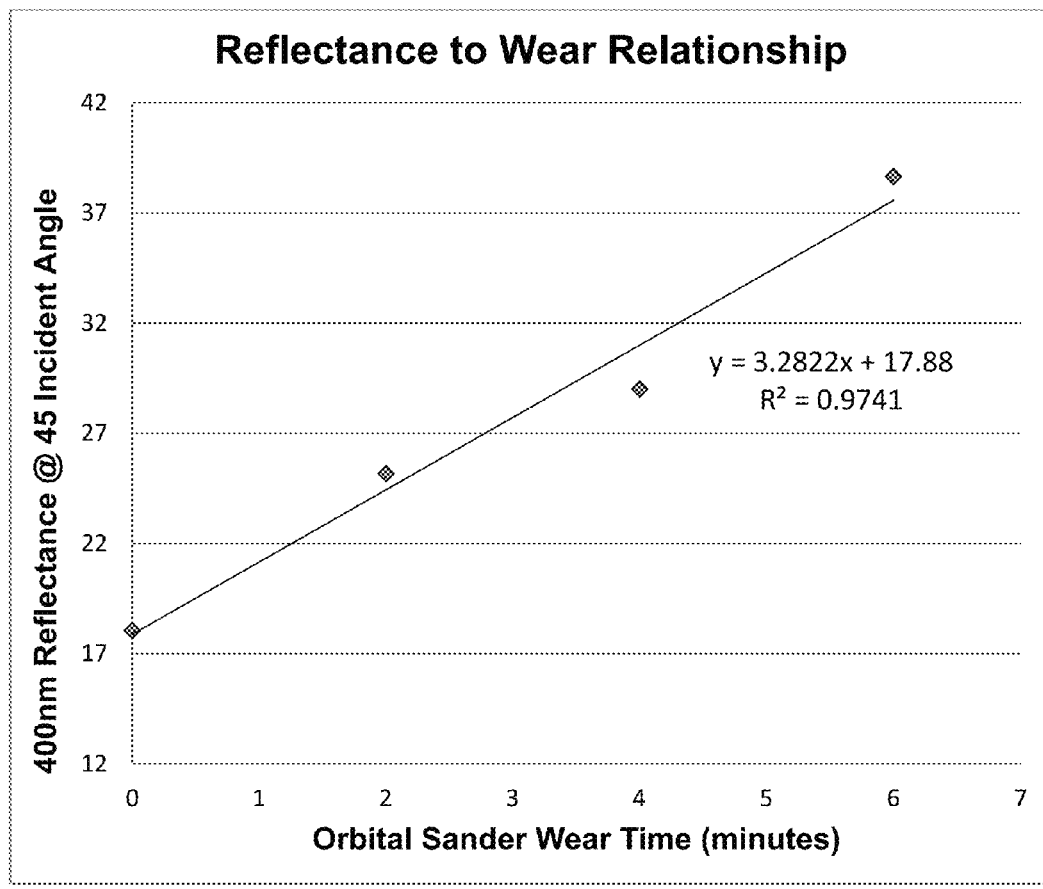
FIG. 2. Reflectance/wear relationship; increasing reflectance is observed with increasing wear.

For this series of tests we cut a single ply sample of fabric from the leg of the MCCUU trouser that was approximately 16 in$^2$ (103 cm$^2$) and mounted it to a wooden block. Using an orbital sander with mild grade sandpaper, we abraded the surface of the MCCUU to varying amounts as a function of time. All of the abraded and non-treated control samples were then washed in a commercial washing machine to remove any residual abrasion debris. The 45° reflectance spectrum of each sample was then measured using Ocean Optics Red Tide USB650 UV/VIS/NIR spectrometer attached to an R400-7-VIS-NIR reflectance probe over a range from 350-1000 nm. We found a strong linear correlation between the abrasion time and reflectance at 400 nm of the fabric (FIG. 2).

Figure 3:
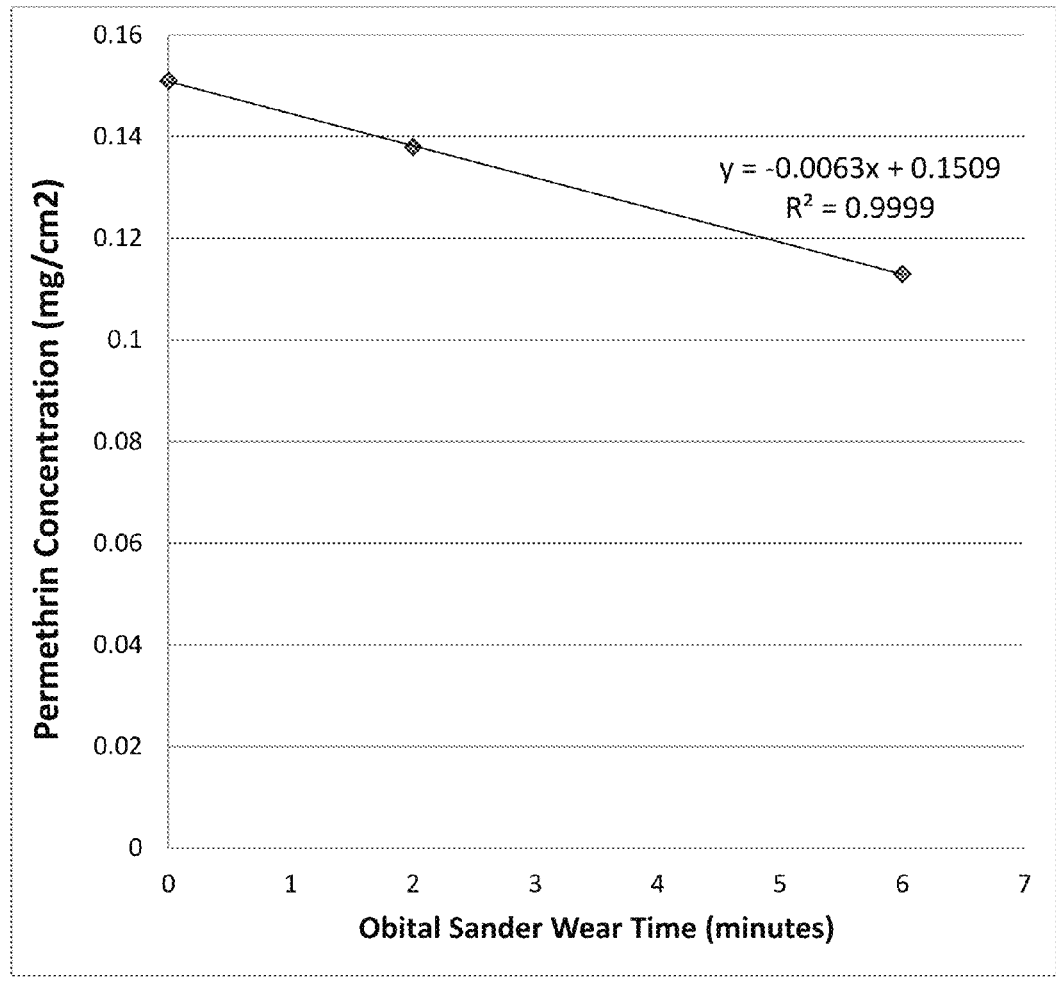
FIG. 3. Permethrin concentration/wear relationship; permethrin levels decrease with increasing wear.

Those measured samples were then cut to 25 cm$^2$ and then Soxhlet extracted with ethyl acetate. The extracted solution was analyzed using a Shimadzu GC-2010 gas chromatograph (GC) with an electron capture detector (ECD-GC) to quantify the amount of remaining permethrin on the fabric. Again, we observed a strong linear correlation between the abrasion time and amount of permethrin remaining in the MCCUU samples (FIG. 3).

Figure 4:
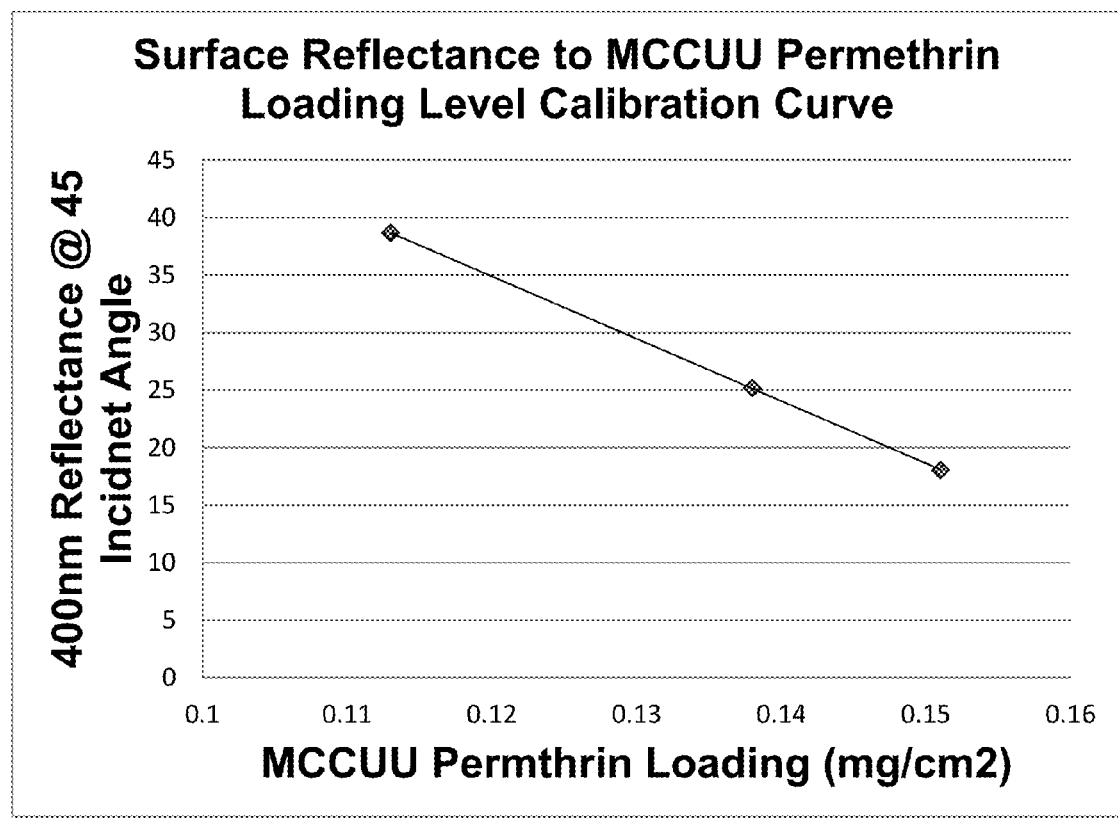
FIG. 4 Surface reflectance of MCCUU vs. permethrin loading level (calibration curve).

The correlation between the reflectance of the worn MCCUU and the amount of permethrin remaining was established; this relationship is shown in FIG. 4. To demonstrate the usefulness of this calibration curve, we also abraded a fabric sample with a belt sander. This method produced an unknown level of wear in the MCCUU sample, thus we used the reflectance measurement from this unknown to estimate the amount of permethrin remaining on the surface from the calibration curve shown in FIG. 4. We then quantified the amount of permethrin in the unknown sample to establish the accuracy of our nondestructive permethrin quantification method. For the belt-sanded, unknown sample, the reflectance measurement predicted 0.132 g/cm$^2$ permethrin remaining; we quantified 0.129 g/cm$^2$ permethrin in that sample. This represents a difference of 0.003 g/cm$^2$ which is a relative error of 2.32%. Such precision is more than sufficient for practical purposes.

Example 2

This example demonstrates the relationship between optical measurements and the loss of bite protection in a treated MCCUU fabric as the uniform is worn. Bite protection is based on two fundamental properties of a fabric; the first is the amount of bio-available permethrin insecticide on the surface of the fabric and the second is the physical barrier to biting insects that prevents them from biting the wearer. Both of these properties are affected by the abrasion and wear a uniform sustains during its life cycle. In this example optical measurement techniques are used on field-worn uniforms to establish a correlation with their protective performance. Below, we describe both the techniques we used to characterize the surface of the fabrics and the optical transmission properties.

Optical measurement analysis was first performed using data from Faulde et al., 2006 (Michael K. Faulde, "Factory-Based Permethrin Impregnation of Uniforms" Military Medicine, 171, 6:472, 2006; incorporated by reference herein), from new factory-impregnated permethrin battle dress uniforms (BDUs) provided to the German Contingent of the Implementation Forces Afghanistan (ISAF) within the Kabul area. Faulde, 2006 is incorporated by reference herein. The uniforms were field-worn for 3-6 months and washed every 1-2 days. The uniforms that were either worn-out or damaged after 70 to 100 launderings were analyzed for quantification of residual amounts of permethrin and remaining residual knockdown activity.

The published images from Faulde et al. (FIG. 3 in, Faulde, 2006) shown in FIG. 5, were analyzed using fractal dimension analysis (described in greater detail below). The images from Faulde are two-tone (pure black/pure white) and are suitable for a box-dimension fractal analysis. Using this fractal dimensional analysis, we estimated the amount of permethrin remaining based on the change in fractal dimension of the magnified images of the fabric samples. The results are shown in FIG. 6. Results from our analysis of the images shown in Faulde et al., (2006), clearly show a strong relationship between the fractal dimension of the fabric surface and the residual permethrin remaining on the surface.

Fractals can be roughly subdivided into two categories; self-similar and self-affine. Self-similar fractals apply primarily to geometric shapes and self-affine fractals apply to responses to time. Self-similar phenomenon or mathematical sets exhibit a repeating pattern that displays at every scale. If the replication is exactly the same at every scale, it is called a self-similar pattern In the fractal analysis method used in the current application the box-counting dimension, (a way of determining the fractal dimension of a set "S" in an image). The photographic image of a fabric sample is first converted to a two-tone image (pure black/pure white). This process is known in the digital arts as "posterizing", and is generally defined as the conversion of an image having a continuous gradation of colors or greyscale to several regions of fewer tones, often only a small number of tones, with abrupt changes from one tone to another. This method was originally performed with photographic processes to create posters. It can now be done with digital processing software. For fractal analysis the posterization of the image takes it down to the minimum number of tones: only pure black and pure white (for example see FIG. 7 and FIG. 8). To calculate this dimension for the fractal "S", the black and white (posterized) image is analyzed by placing a square grid pattern of evenly-spaced gridlines over the image, and then counting how many boxes are required to cover either all of the white or black portions of the image. The box-counting dimension is calculated by quantifying how this number of boxes changes as the boxes become smaller (or the grid becomes finer). In particular, N($\epsilon$) is defined as the number of boxes of side length $\epsilon$ required to cover the set, and the box-counting dimension can be defined as:

$$\dim_{box}(S) := \lim_{s \to 0} \frac{\log N(\varepsilon)}{\log(1/\varepsilon)}.$$

In practice the process may be simplified by a graphical approach where one (either a person drawing the boxes by hand, or more preferably, one of many available software programs that perform this function digitally) initially defines a box dimension where boxes are placed at any position and orientation to minimize the number of boxes needed to cover the fractal object. In other words, the grid is rotated until the number of required boxes to cover the selected color (white or black) is minimized. One counts the number of boxes (N(d)) of linear size d necessary to cover the set for a range of values of d; and plots the logarithm of N(d) on the vertical axis versus the logarithm of d on the horizontal axis. If the object is fractal, the plot will follow a straight line with a negative slope that equals the fractal dimension. To obtain points that are evenly spaced in log-log space, it is best to choose box sizes d that follow a geometric progression (e.g., d=1, 2, 4, 8, . . . ), rather than use an arithmetic progression (e.g., d=1, 2, 3, 4, . . . ). In practice, for each box size, the boxes (a grid) should be overlaid in such a way that the minimum number of boxes is occupied. This is accomplished by rotating the grid for each box size through 90 degrees and plotting the minimum value of N(d).

Figure 5:
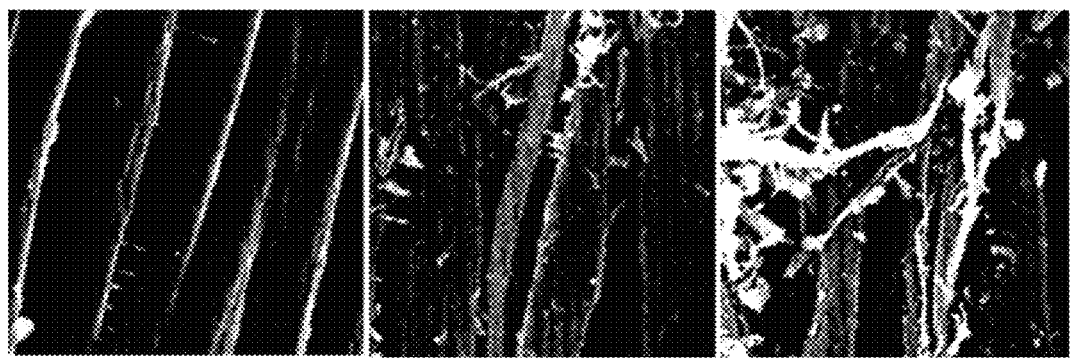
FIG. 5. Microscopic images from Faulde et al., 2006, left is prior to laundering, center is worn-out during deployment with residual permethrin 560 mg/m$^2$, right is worn out during deployment and dry cleaned, yielding a residual permethrin level of 13 mg.
Figure 6:
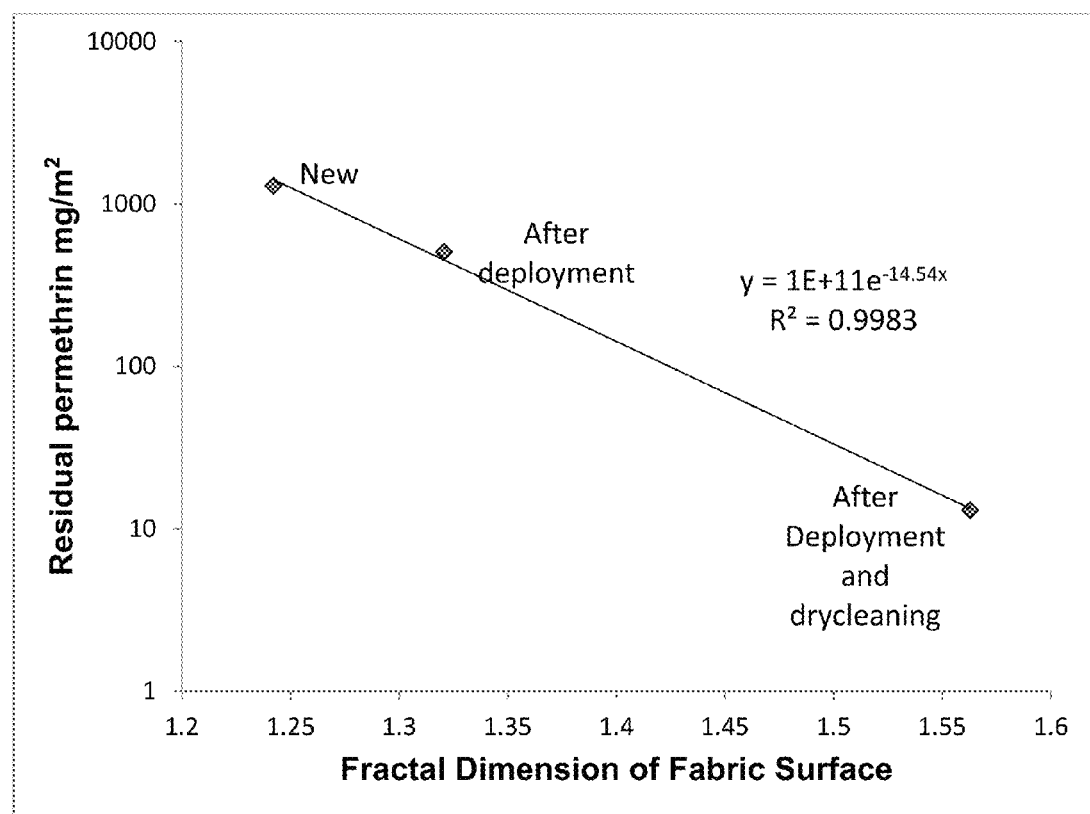
FIG. 6. Residual permethrin vs. fractal dimension of fabric sample.
Figure 9:
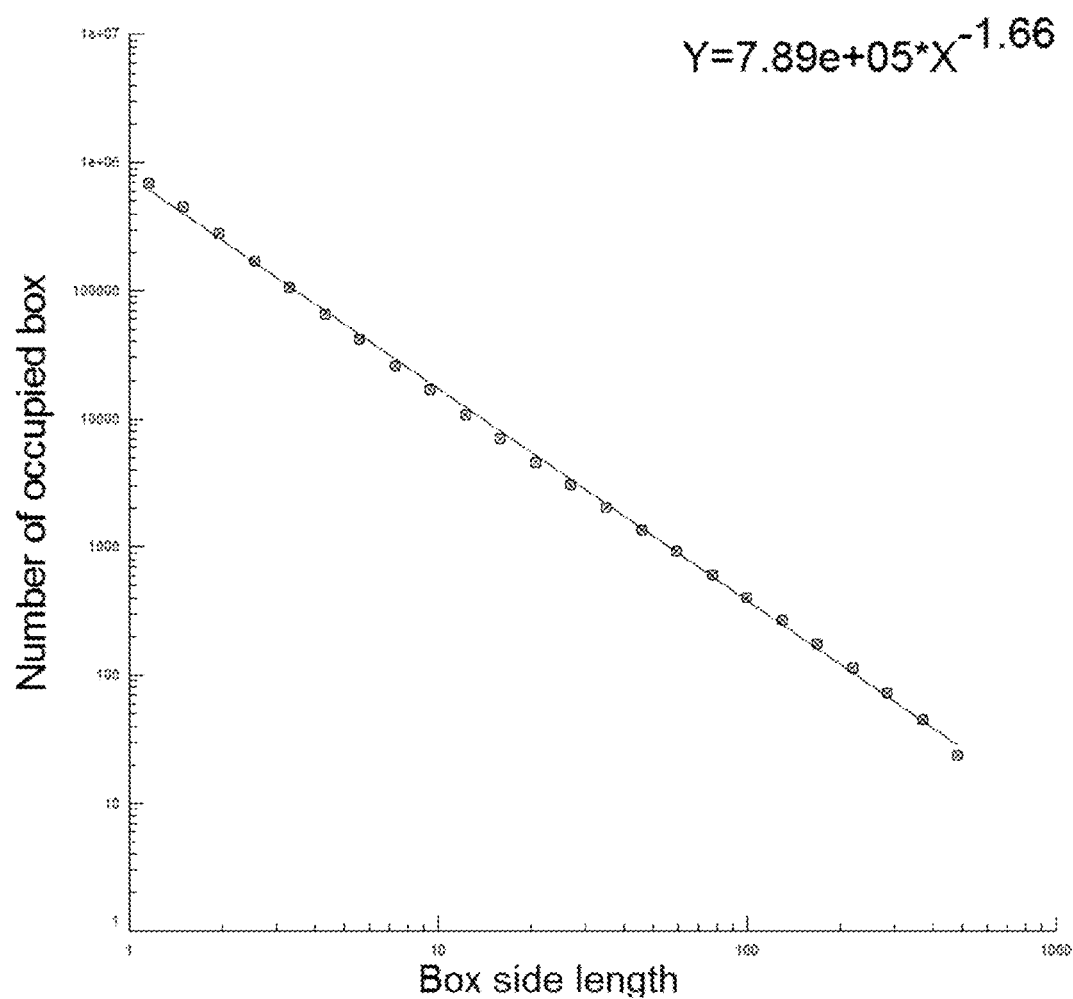
FIG. 9. Fractal dimension (slope of line) estimate from slope of boxes occupied vs. the box length.

FIG. 9 shows a plot the number of boxes occupied versus the box length for a black and white image in FIG. 5 (left panel). On the log-log plot the number of boxes occupied versus the box length is linear indicating the fractal nature of the fabric surface and the fractal dimension given by the slope is 1.66 (the inverse of the slope is generally used).

In addition, worn MCCUU samples were obtained and used with the fractal analysis method. First, the surface of the field-worn fabrics were imaged and these images were analyzed to establish correlations to bite protection and the measured level of permethrin remaining. We utilized both an optical microscope (Olympus BX40 system microscope with a PAXCAM 5 digital camera; multiple magnifications were used but 5× was used for the analysis described below) and a smartphone with a microscopic lens adaptor (Olloclip® Macro 3-in-1 Lens, 21× magnification). A preferred method used a smartphone and attached microscope (FIG. 1). It is understood that an app could be written to take data from the camera, and with the appropriate algorithm calculate the uniform's protective capacity remaining.

Figure 7:
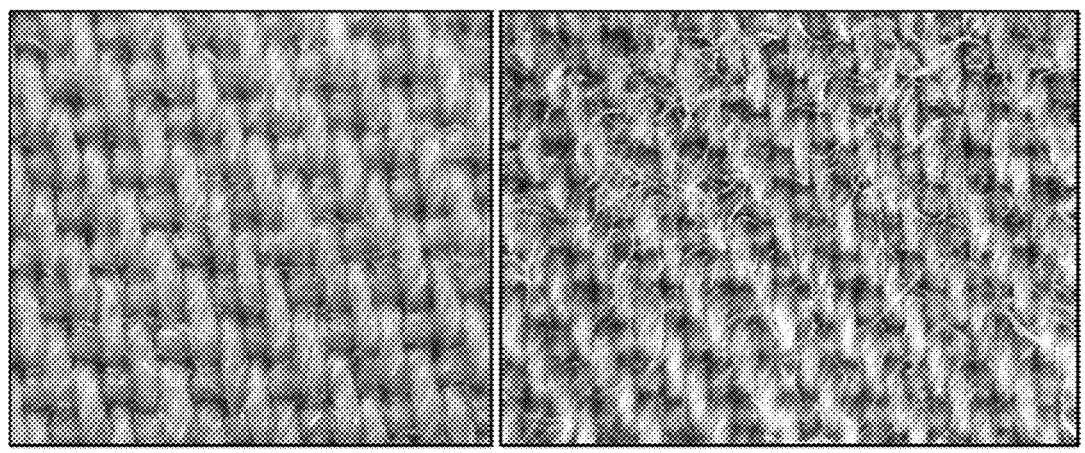
FIG. 7. Magnified images (taken with a smart phone and a micro-lens adapter) of field worn MCCUU fabrics. The sample in the image on the left has been exposed to a lower level of abrasion compared to the sample on the right.
Figure 8:
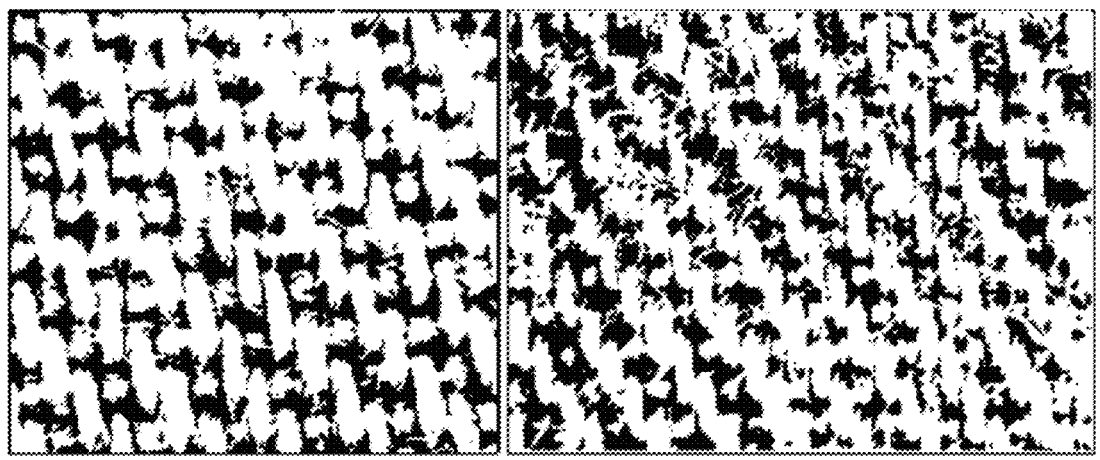
FIG. 8. Posterized (digital transformation) image from FIG. 7.

Examples of the smartphone images that were taken of the uniform fibers are shown in FIG. 7. The fabric sample on the right of FIG. 7 has experienced more surface abrasion than the fabric on the left. The torn, broken fibers are in the photograph on the right, and the loss of those fibers (that would be coated with permethrin) would indicate a reduction in the protective capacity of the MCCUU fabric. To quantify and measure the difference in these field worn MCCUU fabric samples, five images were taken at randomly selected locations from each of the fabric samples. The images were evaluated with a fractal analysis algorithm (BENOIT™; Trusoft Intl., Inc.) using a box counting analysis method to determine the fractal dimension. Fractal dimension is an index for characterizing patterns and quantifying their complexity; as new fabric sample becomes worn the repeatable fabric pattern is broken up and the fractal dimension becomes smaller. As can be seen in the images, the sample on the right of FIG. 7 has structure broken up by the abraded surface fibers, thus changing its fractal dimension compared to a new pristine uniform surface.

Figure 10:
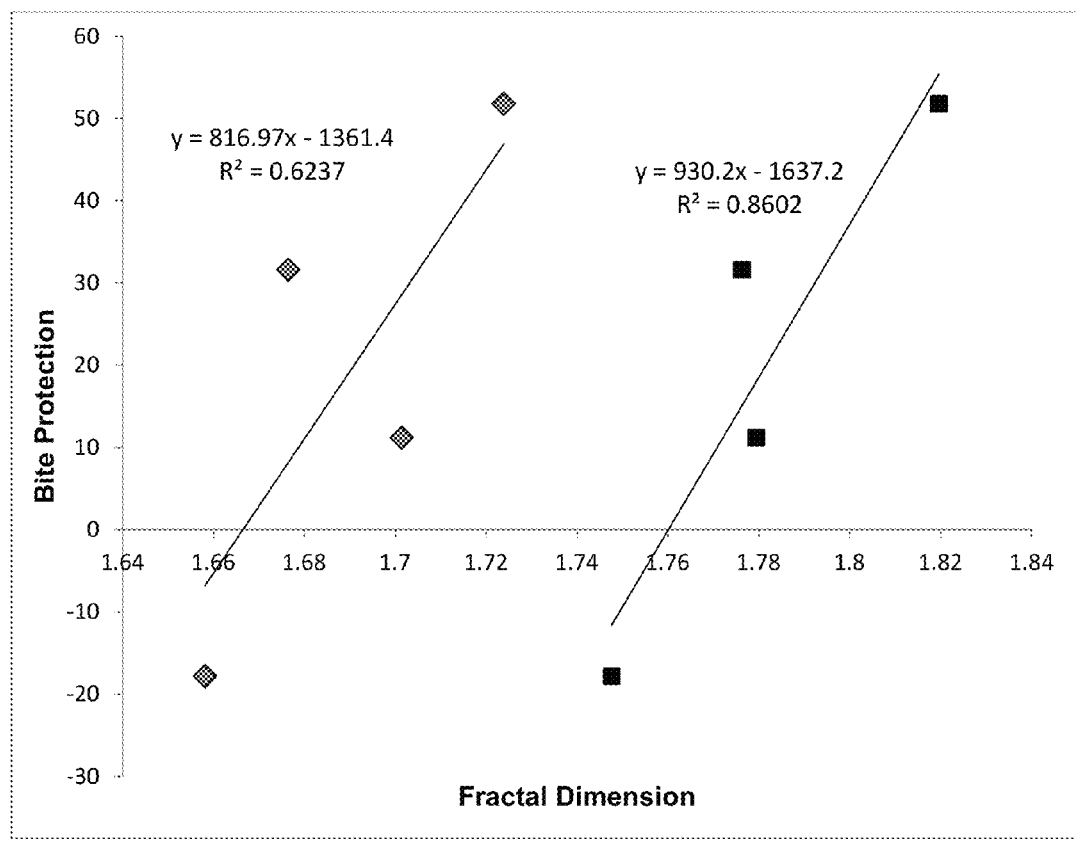
FIG. 10. Fractal dimension to bite protection correlation. Black square data points obtained from the smartphone images (right) and grey diamond data points from 5× magnification (left).

Images from both the microscope and smartphone were analyzed to determine the correlation with bite protection and retained permethrin. There is a clear correlation between the bite protection and fractal dimension measured for the different uniforms; these correlations are shown in FIG. 10. The microscope and smartphone images were taken at different locations.

The field-worn uniforms have been analyzed for permethrin content. We also calculated the correlation between the measured fractal dimensions and the amount of permethrin on the samples. To test how well our correlation predicted the result, the measured fractal dimensions of the fabric samples were then entered into the calibration curve predicted by the correlation and the results were plotted against the actual measured permethrin content, as discussed below.

Loading quantification on treated uniforms utilized an electron-capture detector (ECD) gas chromatograph (GC). The Shimadzu GC-2010 was equipped with a 30 m×0.25 mm (0.25 µm film thickness) ZB-5 capillary GC-column (Phenomenex, Torrance, Calif.). The ECD detector is the preferred detector for the quantification of most insecticides/repellents, including pyrethroids, and when coupled with the ZB-5 GC-column (which is capable of separating stereoisomers of most pyrethroids).

To quantify of the amounts of repellent loaded onto fabric samples, we first Soxhlet extracted treated fabric swatches with ethyl acetate solvent for 6 hours in order to completely remove the insecticide. Once the swatch was extracted, the ethyl acetate extraction solution was diluted with hexanes to 200 mL. This extraction solution is then analyzed by gas chromatography (GC) to both verify the composition of the repellent via chromatographic retention time ($R_t$) and to quantify the amount of repellent that was washed off of the fabric sample. GC is ideal for this application since it separates the multiple compounds that may be washed out of the fabric and allows us to specifically identify and quantify the insecticide.

The extracted insecticide in the solution is then quantified using standard GC calibration curves of GC-peak area vs. concentration that have been developed from known concentration standard solutions of the repellents.

Figure 11:
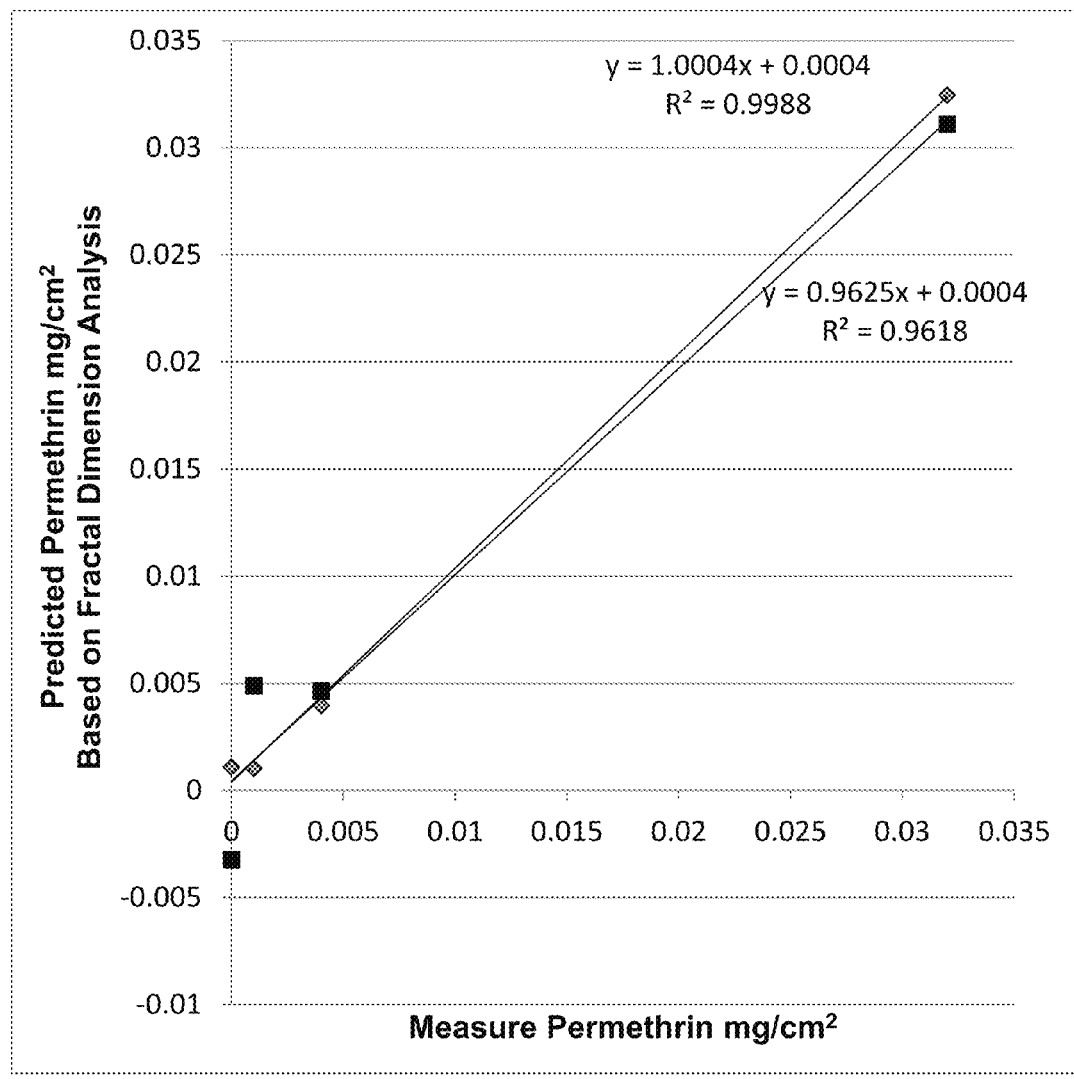
FIG. 11. A plot of the predicted permethrin concentration based on fractional dimensional analysis compared to the actual measured permethrin content of the field worn MCCUU uniforms. The smartphone, black square data points and microscope, grey diamond data points from 5× magnification, have good correlation near 1.0.

The plots for both the microscope and smartphone images are shown in FIG. 11. With a perfect correlation between the actual and predicted permethrin values, the plots in FIG. 11 should have a slope of 1 and a correlation coefficient ($R^2$) of 1. As can be seen, for both sets of data, the slope and $R^2$ are nearly 1 (again, the smartphone camera data correlates better than the microscope images), indicating a good quantitative method for determining the amount of permethrin remaining in the samples.

Figure 12:
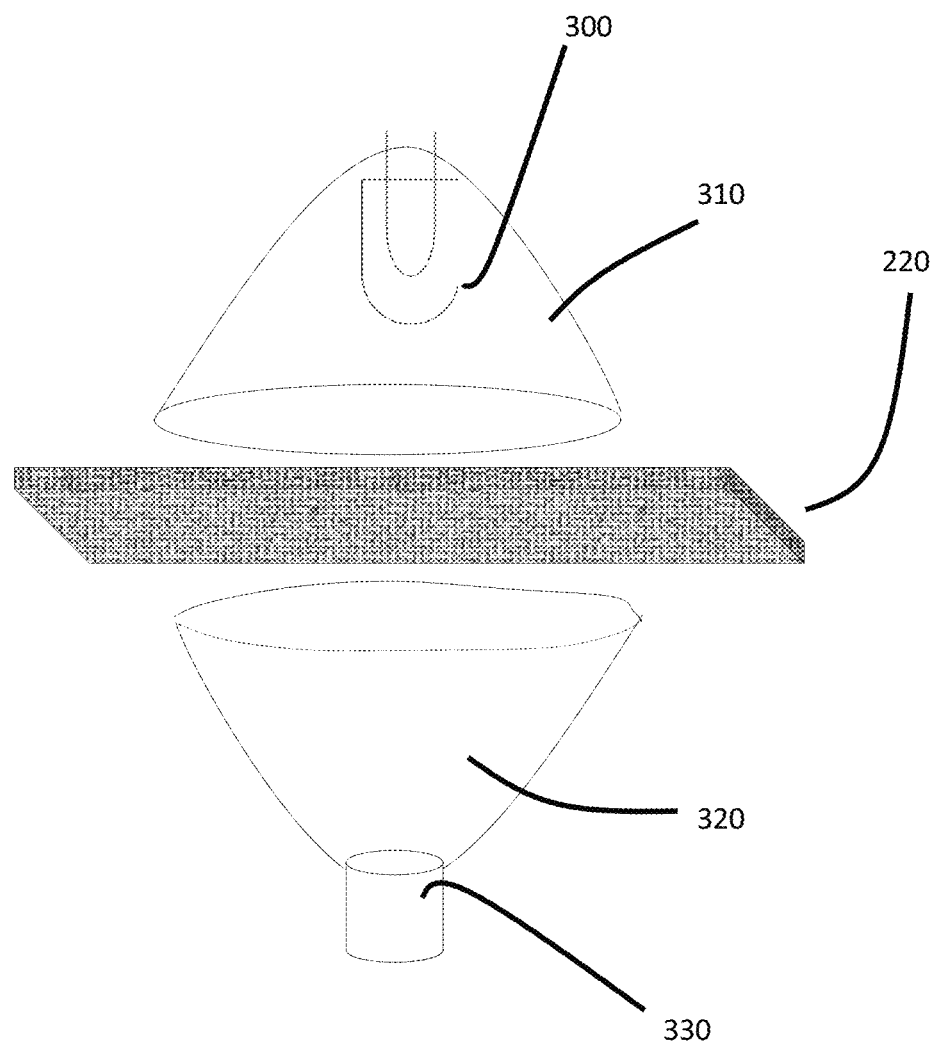
FIG. 12. Optical transparency measurement device, LED flashlight for a light source [300], reflector [310] and a collector [320] and a TAOS light-to-digital converter [330] to measure light passing though the fabric sample [220].

Example 3 predicting bite protection based on light transmission through field-worn samples. As the bulk weave of the fabric loosens and the gaps between the fibers increase, it is easier for the insects to bite through the uniform. The optical amount of light that passes through the uniform will increase as the fabric density decreases, opening small orifices for light to pass through. We measured the optical transparency of the field-worn MCCUU samples using a 3-watt white LED from a flashlight and a TAOS light-to-digital converter (TCS3472, TAOS, Plano, Tex.). The device used to make the measurements is shown in FIG. 12.

Figure 13:
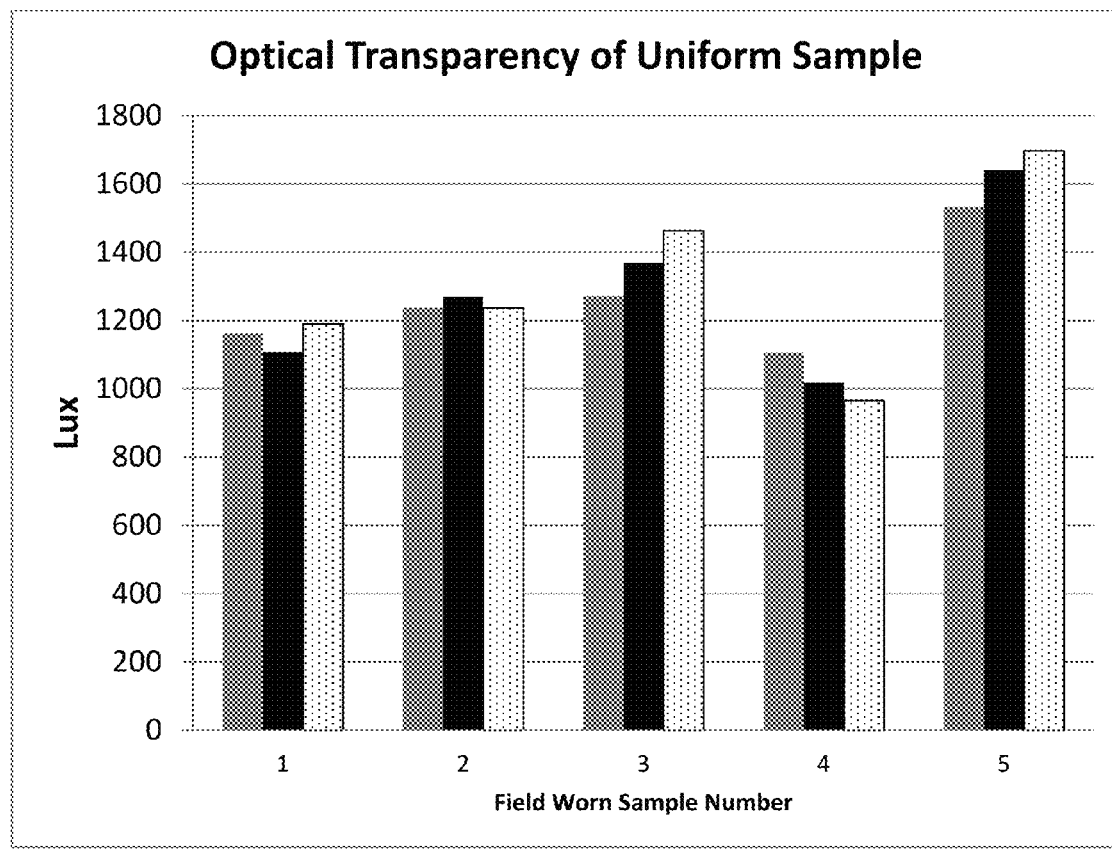
FIG. 13. Optical transparency (Lux) for three color regions in fabric samples. Grey is the blue spectrum, black is the red spectrum and dotted is the green spectrum.

The area sampled was about 3.5 inches in diameter, encompassing a majority of the fabric sample. Approximately equal amounts of the different camouflage coloring were present in each of the sampled areas. Three replicates measurements were made on each sample. The data for the three replicates of the five samples is shown in FIG. 13. There are differences in the fabrics samples, suggesting differences in the level of wear each of the field worn uniforms have experienced.

Figure 14:
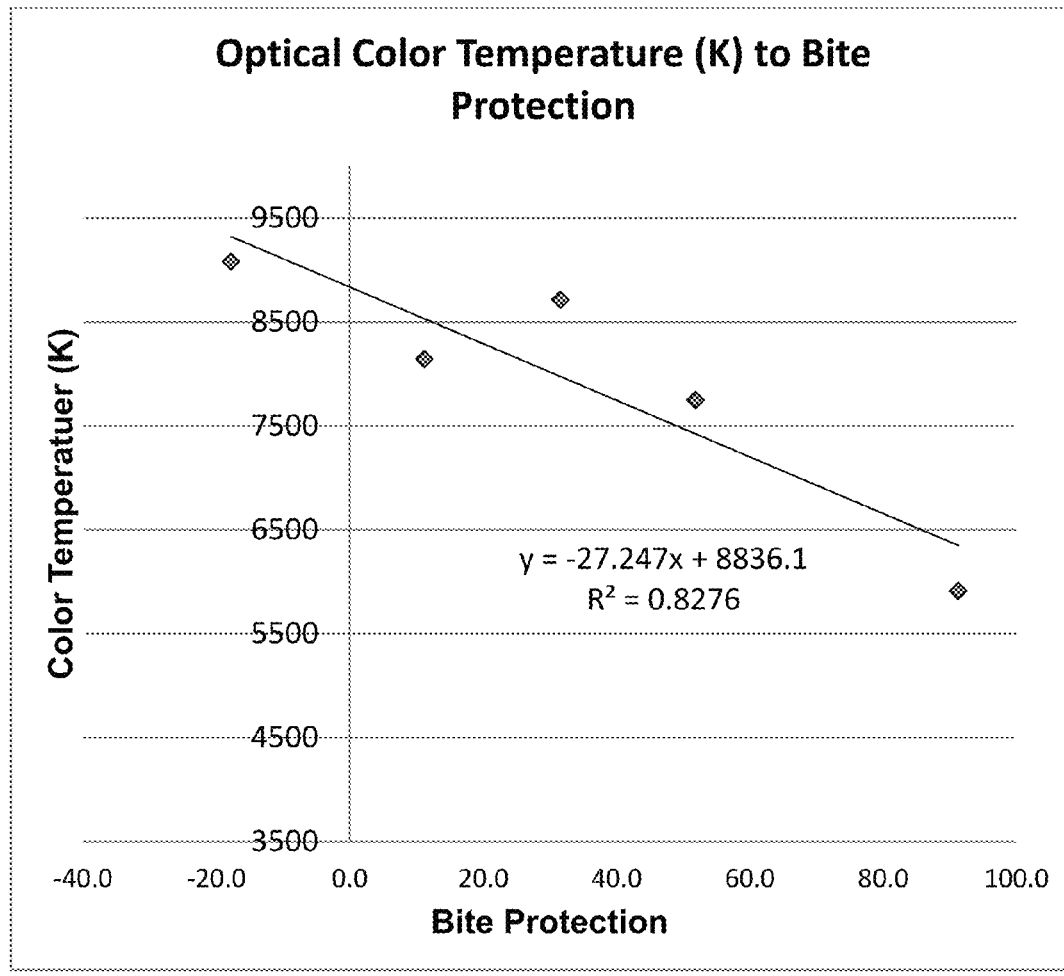
FIG. 14. Color temperature (K) vs. the measured bite protection of field-worn uniforms.

Analysis showed a correlation between overall luminance and bite protection. However, we found an even stronger correlation between the color temperature and bite protection (FIG. 14). There is a clear, observable difference in the measured color temperature with a direct, linear correlation to the fabric's measured bite protection. When light passes through the fabric, not only is the light intensity reduced, but the light spectrum is shifted by differential absorption of light wavelengths in the fabric. one could use a spectrophotometer to record and analyze the full spectrum. For example, a smartphone camera and currently available software to analyze the light spectrum. In this example a sensor that breaks the spectrum into red, green and blue components was used to demonstrate the method. The software for this sensor calculates both light intensity and color temperature, as a simple metric for the spectrum of visible light. The color temperature of a light source (in Kelvin) is the temperature of an ideal black-body radiator which closely matches the color of the light source. Examples of color temperatures include 2800K for a household incandescent lamp to 5000K for a fluorescent lamp, while an overcast day can be 6500K. The color temperature effectively captures the spectral shift caused by light absorption in the new or worn fabric. Optionally, one embodiment of the invention the color temperature can be quantified by determining the wavelength of light in the full spectrum that has the highest intensity, and then using that wavelength to quantify the color temperature of the light source.

Example 4

Bifenthrin treated uniforms: This example illustrates the method of the present invention when using bifenthrin as the insecticide, or active ingredient, in the functional fabric. Samples of Army Combat Uninforms (ACUs) treated with bifenthrin were used in this example.

Six ACU uniforms (jackets and trousers) that were previously treated with bifenthrin were used for textile washing experiments and then cut into fabric samples for both bifenthrin loading determination and mosquito efficacy testing. After the washing procedure, the samples fabric swatches were cut from locations around treated ACU jackets and trousers that included both the front and back of the uniform.

These uniforms had an original loading of bifenthrin of 0.135-0.176 mg/cm$^2$. The textile samples were divided into 7 groups and washed either, 0, 1, 5, 10, 25, 40 or 50 times according to the procedure outlined in AATCC Test Method 135-2004. Samples of these uniforms at each wash level were analyzed to quantify the amount of the bifenthrin on the treated uniforms. Samples were also prepared for mosquito knockdown (KD) testing in order to assess the efficacy of the treated uniforms. Bifenthrin content was determined by Soxhlet extraction followed by quantification by GC.

Knockdown testing was conducted by observing knockdown (KD) of *Aedes aegypti* mosquitoes that come into contact with the repellent-treated fabric samples. The knockdown tests briefly expose mosquitoes to samples of the treated fabric and then quantify mortality and immobilization of mosquitoes for 1 hour following exposure to the sample; the number of mosquitoes that die or are immobilized (i.e., "knocked down") is then recorded and reported as a percent. All KD tests were performed at 20-22° C. using adult, non-blood-fed female *Aedes aegypti* mosquitoes that were 5-15 days old were used for the testing.

KD testing was performed by exposing *Ae. Aegypti* to the treated fabric sample for two minutes, then removing the treated fabric sample and monitoring the mosquitoes for incapacitation and mortality (i.e., "knockdown"). The number of mosquitoes knocked-down (dead or incapacitated) was recorded at 15 minutes after the initial two-minute fabric exposure and reported as a percentage of the total number of mosquitoes in the test. Each KD value reported is an average of three separate KD tests with 3 different fabric swatches from various locations around the ACUs, and includes samples from both trousers and coats at the different washing levels.

Figure 15:
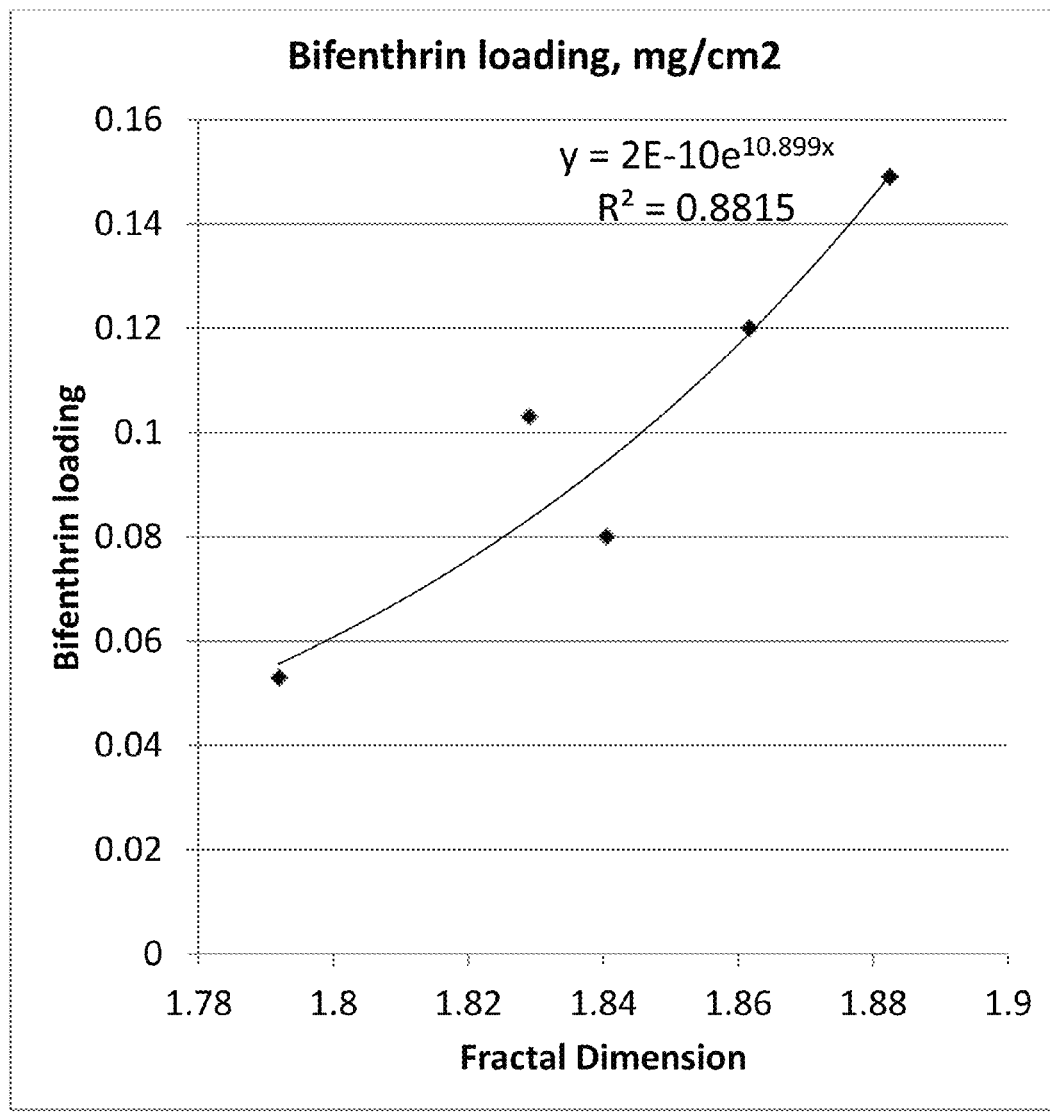
FIG. 15. Bifenthrin loading vs. fractal dimension of functional fabric samples.
Figure 16:
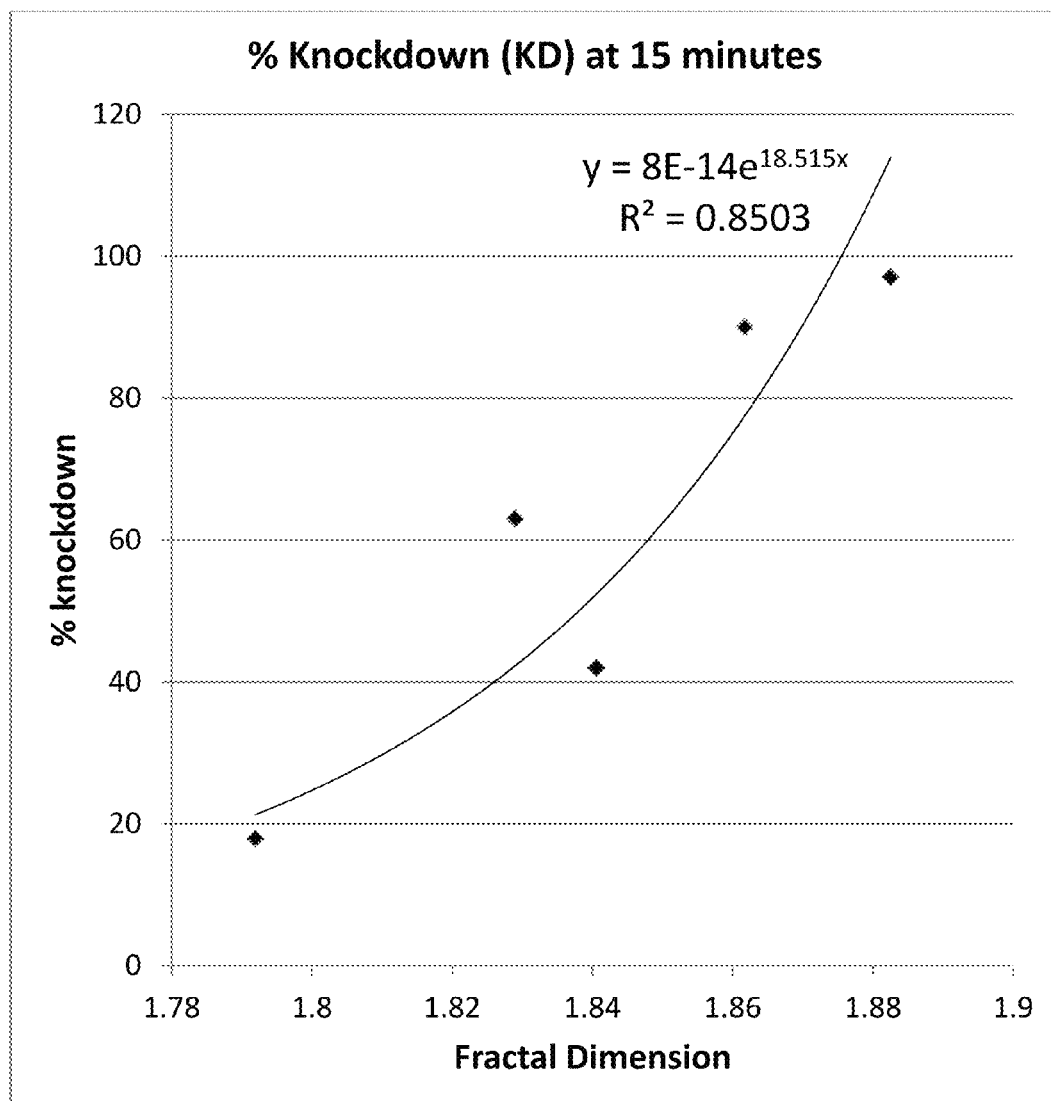
FIG. 16. Percent knockdown vs. fractal dimension for worn functional fabric samples.
Figure 17:
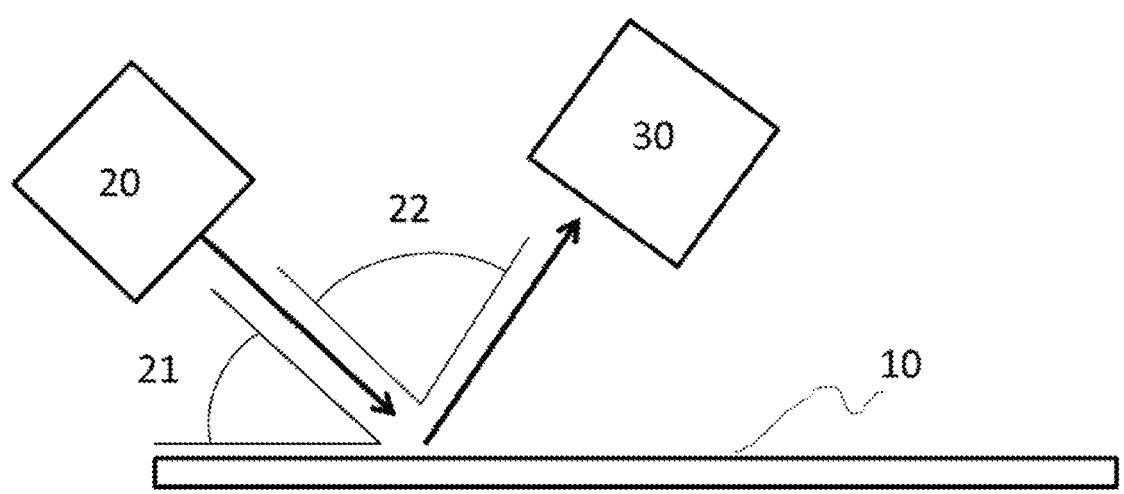
FIG. 17. Measuring reflectance of functional fabrics.
Figure 18:
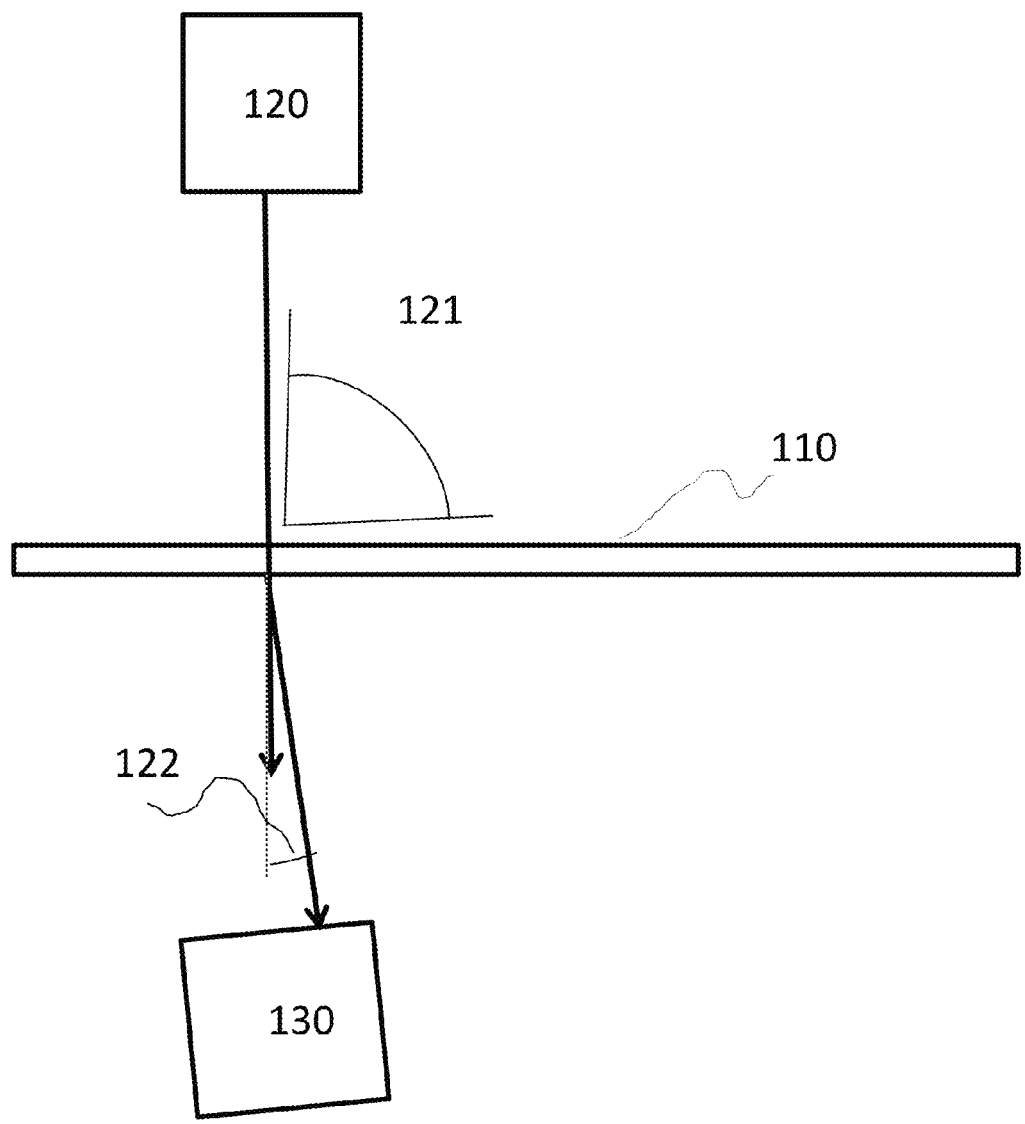
FIG. 18. Measuring transmittance of functional fabrics.
Figure 19:
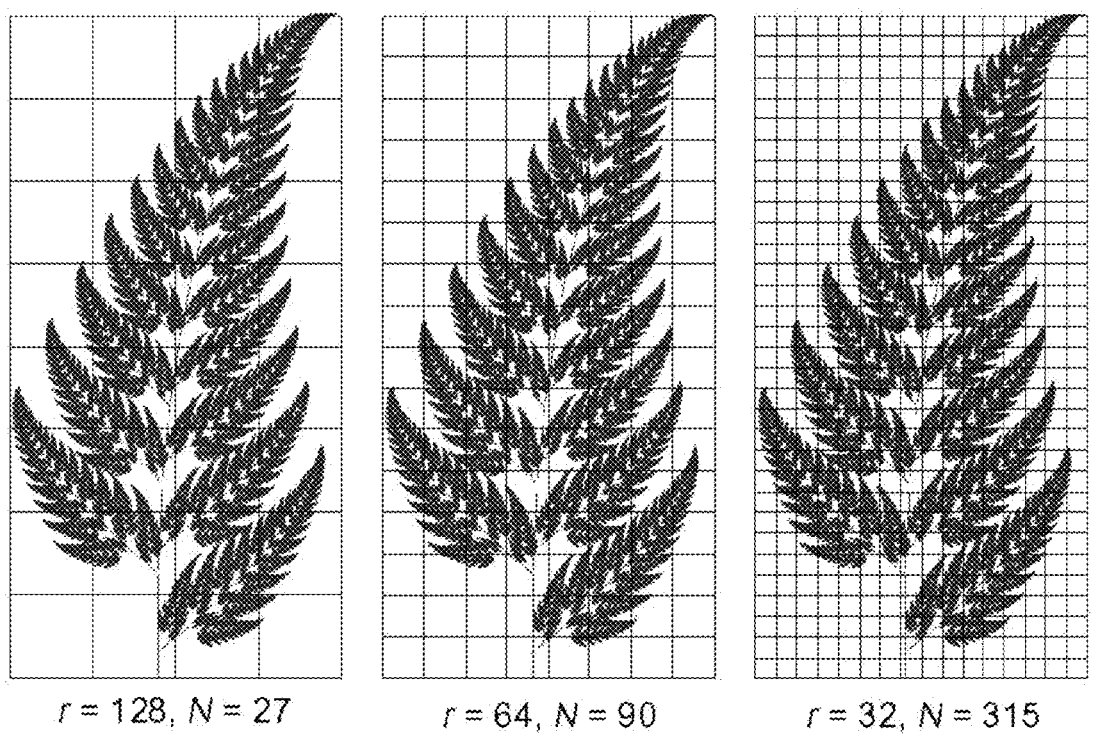
FIG. 19. Example of the box-method for evaluating a fractal image from Barnsley M. (1988) "Fractals Everywhere" New York: Academic Press.

Digital images were taken using a smart phone with a microscopic lens adaptor having 21× magnification. The images were converted to pure tone black/white (posterized) images and analyzed using the fractal analysis software described previously. Again, this fractal analysis determines the fractal dimension (box dimension method). A calibration curve was established for to the relationship between the fractal dimension and the functionality (observed knockdown). The fractal dimension was evaluated for six samples and then these values were averaged and used to make the calibration curves. FIG. 15 shows the fractal analysis method to develop the calibration curve that can be used to quantify the functionality of worn or laundered functional fabrics. FIG. 16 shows an analogous method to evaluate the concentration of bifenthrin left in functional fabrics.

The present invention provides a method using a field assay that, in one embodiment, uses a smartphone camera to image the surface of a fielded uniform. That image is them processed using an app which then calculates the amount of insecticide present on the surface. An additional, optional step comprises shining a light through the fabric surface to measure the physical barrier the uniform presents to a biting insect. These two measurements may then be used to determine if a uniform has the required protection against biting insects.

Alternatively, since both transmission and surface abrasion are ultimately determined by the degree of wear, the camera images alone can be used (i.e., it is proportional both to surface fraying and the reduction in the physical barrier) to determine the protective capacity of the uniform. If so, the user would only need to make one type of optical measurement.

Although the present invention has been described in considerable detail with reference to certain preferred versions thereof, other versions are possible. For example, other light sources, detector or microprocessors are possible. Therefore, the spirit and scope of the appended claims should not be limited to the description of the preferred versions contained herein.

The reader's attention is directed to all references which are filed concurrently with this specification and which are incorporated herein by reference.

All the features in this specification (including any accompanying claims, abstract, and drawings) may be replaced by alternative features serving the same, equivalent or similar purpose, unless expressly stated otherwise. Thus, unless expressly stated otherwise, each feature disclosed in one example only of a generic series of equivalent or similar features.

Any element in a claim that does not explicitly state "means for" performing a specified function, or "step for" performing a specific function, is not to be interpreted as a "means" or "step" clause as specified in 35 U.S.C. §112 ¶6 or 35 U.S.C. §112(f).

What is claimed is:

1. A method for determining functionality remaining in a functional fabric, the method comprising the steps of:
    (a) providing a used functional fabric having a known original functionality, a current wear, and a current unknown functionality, wherein functionality is insect repellency, insect mortality, insect knockdown or antimicrobial activity,
    (b) providing a light source,
    (c) providing a detector,
    (d) optically measuring the current wear using the light source and the detector, and
    (e) evaluating the current unknown functionality using a correlation that expresses the current unknown functionality versus the current wear.

2. The method of claim 1 further comprising the step of:
(f) aligning the light source, the detector and the functional fabric and measuring reflectance of the light source off of the functional fabric, wherein the light source [20] is aligned relative to the functional fabric [10] at a first angle [21], wherein the first angle is from 0 to 180 degrees; and wherein the detector [30] is aligned relative to the light source at a second angle [22], wherein the second angle is from 0 to 180 degrees, wherein a sum of the first angle plus the second angle is at most 180 degrees.

3. The method of claim 1 further comprising the step of:
(f) aligning the light source, the detector and the functional fabric and measuring a transmittance of the light source through the functional fabric, wherein the light source [120] is aligned relative to the functional fabric [110] at a first angle [121], wherein the first angle is about 90 degrees; and wherein the detector [130] is aligned relative to the light source at a second angle [122], wherein the second angle is from −5 to 5 degrees, wherein a sum of the first angle plus the second angle is at most 180 degrees.

4. The method of claim 3, wherein the optically measuring the current wear using the light source and the detector further comprises a color temperature measurement.

5. The method of claim 1, wherein the light source emits light with a wavelength from 10 nanometers to 100 micrometers.

6. The method of claim 1, wherein the light source emits lights with a wavelength from 10 nanometers to 400 nanometers.

7. The method of claim 1, wherein the light source emits light with a wavelength from 700 nanometers to 100 micrometers.

8. The method of claim 1, where the light source emits light with essentially a single wavelength.

9. The method of claim 1, wherein the functionality is insect repellency or mortality derived from an insecticide or an insect repellent.

10. The method of claim 9, where the insecticide or insect repellent comprises a pyrethroid.

11. The method of claim 10, where the insecticide or insect repellent comprises permethrin.

12. The method of claim 1, wherein the detector further comprises a digital camera, and wherein the method further comprises the step of:
(f) obtaining a magnified image of the functional fabric and quantifying a fractal dimension using a box-method fractal analysis on the image.

13. The method of claim 12 further comprising the step of:
(g) aligning the light source, the detector and the functional fabric and measuring a reflectance of the light source off the functional fabric.

14. The method of claim 12 further comprising the step of:
(g) aligning the light source, the detector and the functional fabric and measuring a transmittance of the light source through the functional fabric.

15. The method of claim 14 further comprising the step of:
(h) measuring the transmittance of the light source through a reference material and quantifying the intensity or spectral distribution of the light source.

16. The method of claim 15, wherein the digital camera is a smartphone, and wherein the step of obtaining an image of the functional fabric and quantifying a fractal dimension using a box-method fractal analysis on the image is performed using the smartphone.

17. The method of claim 16 further comprising the step of:
(g) aligning the light source, the detector and the functional fabric and measuring a transmittance of the light source through the functional fabric.

18. The method of claim 17 further comprising the step of:
(h) measuring the transmittance of the light source through a reference material and quantifying the intensity or spectral distribution of the light source.

* * * * *